(12) United States Patent
Qi et al.

(10) Patent No.: US 10,351,707 B2
(45) Date of Patent: Jul. 16, 2019

(54) WATER-SOLUBLE IRON ION FLUORESCENT PROBE AND PREPARATION METHOD THEREOF

(71) Applicant: CHANGZHOU VOCATIONAL INSTITUTE OF ENGINEERING, Changzhou, Jiangsu (CN)

(72) Inventors: Xiuxiu Qi, Jiangsu (CN); Wenhua Chen, Jiangsu (CN); Bai Chen, Jiangsu (CN); Qiaoyun Liu, Jiangsu (CN); Yaozhong Li, Jiangsu (CN); Wenbin Liu, Jiangsu (CN)

(73) Assignee: CHANGZHOU VOCATIONAL INSTITUTE OF ENGINEERING, Changzhou, Jiangsu (CN)

( * ) Notice: Subject to any disclaimer, the term of this patent is extended or adjusted under 35 U.S.C. 154(b) by 0 days.

(21) Appl. No.: 16/090,637

(22) PCT Filed: Jun. 30, 2016

(86) PCT No.: PCT/CN2016/087965
§ 371 (c)(1),
(2) Date: Oct. 2, 2018

(87) PCT Pub. No.: WO2018/000356
PCT Pub. Date: Jan. 4, 2018

(65) Prior Publication Data
US 2019/0112483 A1  Apr. 18, 2019

(30) Foreign Application Priority Data
Jun. 29, 2016  (CN) .......................... 2016 1 0497836

(51) Int. Cl.
*C09B 11/24* (2006.01)
*C07D 491/107* (2006.01)
*G01N 21/64* (2006.01)
*G01N 33/18* (2006.01)

(52) U.S. Cl.
CPC ............ *C09B 11/24* (2013.01); *G01N 21/643* (2013.01); *G01N 33/182* (2013.01)

(58) Field of Classification Search
None
See application file for complete search history.

(56) References Cited

FOREIGN PATENT DOCUMENTS

CN    104072753 A    10/2014

*Primary Examiner* — Kamal A Saeed
(74) *Attorney, Agent, or Firm* — Novick, Kim & Lee, PLLC; Allen Xue

(57) ABSTRACT

The present invention relates to a water-soluble ferric ion fluorescent probe, and the fluorescent probe molecule has a structure as shown in the following figure. The present invention also discloses a preparation method of the water-soluble ferric ion fluorescent probe.

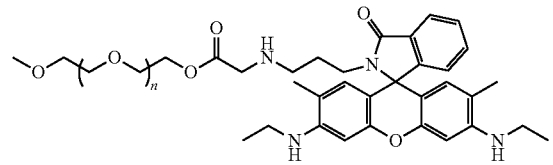

2 Claims, 2 Drawing Sheets

WATER-SOLUBLE IRON ION FLUORESCENT PROBE AND PREPARATION METHOD THEREOF

TECHNICAL FIELD

The present invention belongs to the field of new materials for ion probes and particularly relates to an OFF-ON type ferric ion fluorescent probe and a preparation method thereof, and the probe can be used for the determination of ferric ions in an all-water system.

BACKGROUND ART

Ferric iron is one of the necessary ions in living organisms, which plays a role in transporting and storing oxygen in the body and has extremely important physiological significance. On the other hand, although iron is an essential element of the body, excessive iron in the human body produces excessive oxygen radicals, which may cause damage to the body. Therefore, it is necessary to develop a $Fe^{3+}$ fluorescent probe with excellent performance in order to dynamically detect the content and distribution of $Fe^{3+}$ in a living organism or environment in real time and online. At present, most of the ferric ion fluorescent probes are poorly water-soluble, and a certain proportion of organic solvents need to be added, which greatly limits their application, and particularly limits the use in an aqueous environment containing living organisms because of the lack of such organic solvents in the living organisms. If an organic solvent is additionally added, it may cause damage to living organisms because organic solvents are often toxic. Therefore, there is an urgent need to develop a water-soluble ferric ion fluorescent probe that can be used in an all-water environment.

SUMMARY OF THE INVENTION

An object of the present invention is to provide a synthetic method of a novel OFF-ON type rhodamine derivative water-soluble ferric ion fluorescent probe. This method gives a soluble rhodamine derivative which has a good application prospect in the detection of ferric ion in an all-water environment.

A first aspect of the present invention relates to a water-soluble ferric ion fluorescent probe, and the fluorescent probe molecule has a structure as shown in the following figure:

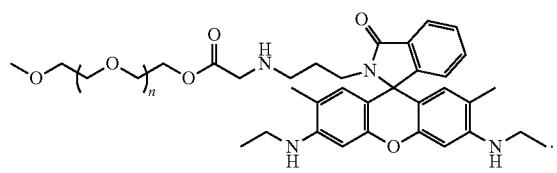

A second aspect of the present invention relates to a preparation method of the water-soluble ferric ion fluorescent probe, including the following steps:

(1) using ethanol as a solvent, adding rhodamine 6G to a concentration of 0.02 mol/L to 0.2 mol/L, adding 1,3-propanediamine and reacting therewith, wherein the molar ratio of 1,3-propanediamine to rhodamine 6G is 0.5:1 to 10:1, controlling the reaction temperature at 40 to 80° C., and reacting for 4-9 h. cooling to precipitate a precipitate, and recrystallizing with acetonitrile to obtain a white crystal A;

(2) using dichloromethane as a solvent, adding methoxy polyethylene glycol MPEG2000 to a concentration of 0.025 mol/L to 0.25 mol/L, adding triethylamine in a molar ratio of triethylamine to methoxy polyethylene glycol MPEG2000 of 10:1 to 1:1, dropwise adding chloroacetyl chloride in a molar ratio of chloroacetyl chloride to methoxy polyethylene glycol MPEG2000 of 10:1 to 1:1, stirring in the dark overnight, precipitating in diethyl ether to obtain a product, dissolving the product in water, adjusting the pH value to 6, extracting 3 times with 20 ml of dichloromethane, and adding diethyl ether and washing to obtain a precipitate B;

and (3) using dichloromethane as a solvent, adding the white crystal A and the precipitate B in a molar ratio of 0.2:1 to 1:0.2, and adding KI in a molar ratio of KI to white crystal A of 0.1:1 to 1:0.1, and adding potassium carbonate of 0.002 mol/L to 0.2 mol/L, reacting for 2-48 h, filtering, and adding the filtrate to diethyl ether to precipitate a precipitate C, and the precipitate C is the water-soluble ferric ion fluorescent probe.

A schematic representation of the reactions involved in the above preparation steps is as follows:

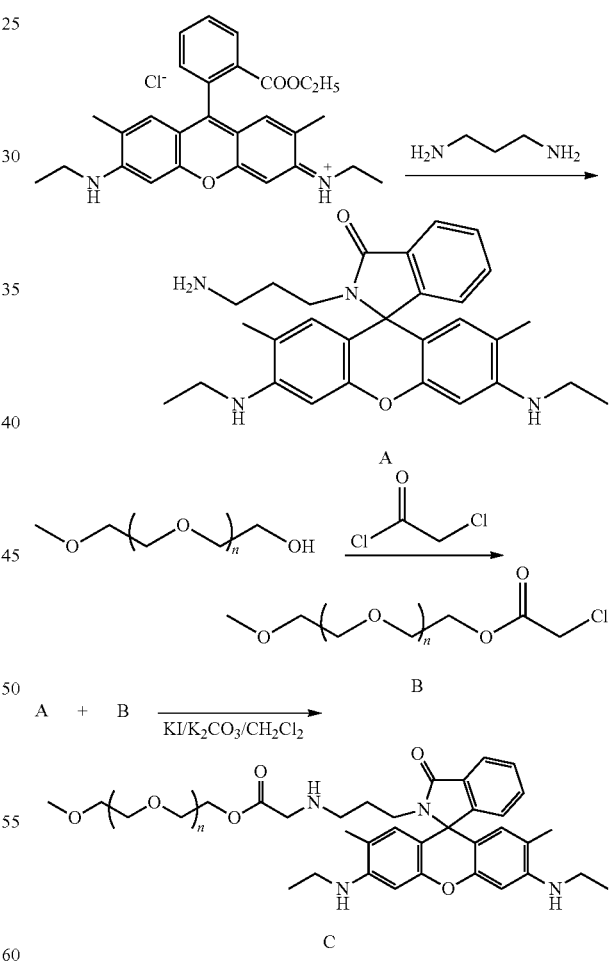

The beneficial effects of the present invention:

1. The water-soluble ferric ion fluorescent probe of the present invention has good water solubility and does not require the addition of an organic solvent when used, which makes it possible to directly measure ferric ion in an aqueous environment containing living organisms.

2. The fluorescent ion probe of the present invention has excellent selectivity to ferric ion, and has good anti-interference ability to common metal ions such as $Fe^{3+}$, $Fe^{2+}$, $Cu^{2+}$, $Zn^{2+}$, $Ni^{2+}$, $Ca^{2+}$, $Cd^{2+}$, $Mg^{2+}$, $Pb^{2+}$, $Hg^{2+}$, $K^+$ and $Na^+$, etc.

3. The detection of ferric ion by the fluorescent ion probe of the present invention can be observed by the naked eye, which does not require complicated instruments.

4. The fluorescent ion probe of the present invention can penetrate the cell membrane and bind to $Fe^{3+}$ in the cell, and can be used for monitoring $Fe^{3+}$ in the internal environment of living cells.

DETAILED DESCRIPTION OF THE INVENTION

Example 1

The preparation method of ferric ion fluorescent probe compound C comprises the following steps:

Synthesis of rhodamine 6G derivative (A): 2 mmol of rhodamine 6G was dissolved in 20 ml of hot ethanol, and 1,3-propanediamine was dropwise added, and the mixture was heated under reflux for 6 h. The solution was cooled to room temperature, and a solid was precipitated and recrystallized with acetonitrile to give a white crystal A. ($^1$H-NMR (CDCl$_3$): δ 7.95 (d, 1H), 7.47 (t, 2H), 7.05 (d, 1H), 6.34 (s, 2H), 6.23 (s, 2H), 3.50 (t, 2H), 3.24 (t, 4H), 2.39 (t, 2H), 1.90 (s, 6H), 1.36 (t, 6H), 1.19 (m, 2H))

Synthesis of methoxy polyethylene glycol chloroacetate (B): 10 g (5 mmol) of methoxy polyethylene glycol (molecular weight 2,000) was dissolved in 20 ml of anhydrous dichloromethane, and 2.09 ml (15 mmol) of triethylamine, 7.95 ml (100 mmol) of chloroacetyl chloride was dropwise added under a N2 atmosphere, and the mixture was stirred overnight in the dark. A product was precipitated from diethyl ether. The product was dissolved in water, adjusted to pH value 6, extracted 3 times with 20 ml of dichloromethane, and added with diethyl ether to precipitate a precipitate B. ($^1$H-NMR (CDCl$_3$) (4.20 (COOCH2), 4.15 (CH2Cl), 3.3-3.7 (OCH2CH2O))

Synthesis of fluorescence probe (C): 10 mg (0.02 mmol) of rhodamine 6G derivative, 4.4 mg (0.026 mmol) of KI, 15 mg (0.11 mmol) of potassium carbonate, 10 mg (0.005 mmol) of PEG, and 5 ml of dichloromethane, were reacted for 10 h under N2, and filtered, and the filtrate was added to diethyl ether to precipitate a precipitate C. ($^1$H-NMR (CDCl$_3$) (δ 7.95 (COCCH), 7.47 (CHCHCH), 7.05 (CHCHC), 6.34 (CCHCC), 6.23 (CCHCO), 4.20 (COOCH2). 4.15 (CH2Cl), 3.3-3.7 (OCH2CH2O, NCH2, OCH3), 3.24 (CH2CH3), 2.39 (NHCH2), 1.90 (CCH3), 1.36 (CH2CH3), 1.19 (NCH2CH2))

Example 2 Performance Experiment of Ferric Ion Fluorescent Probe Compound

1) Selectivity of the Ferric Ion Probe

Figure 1:
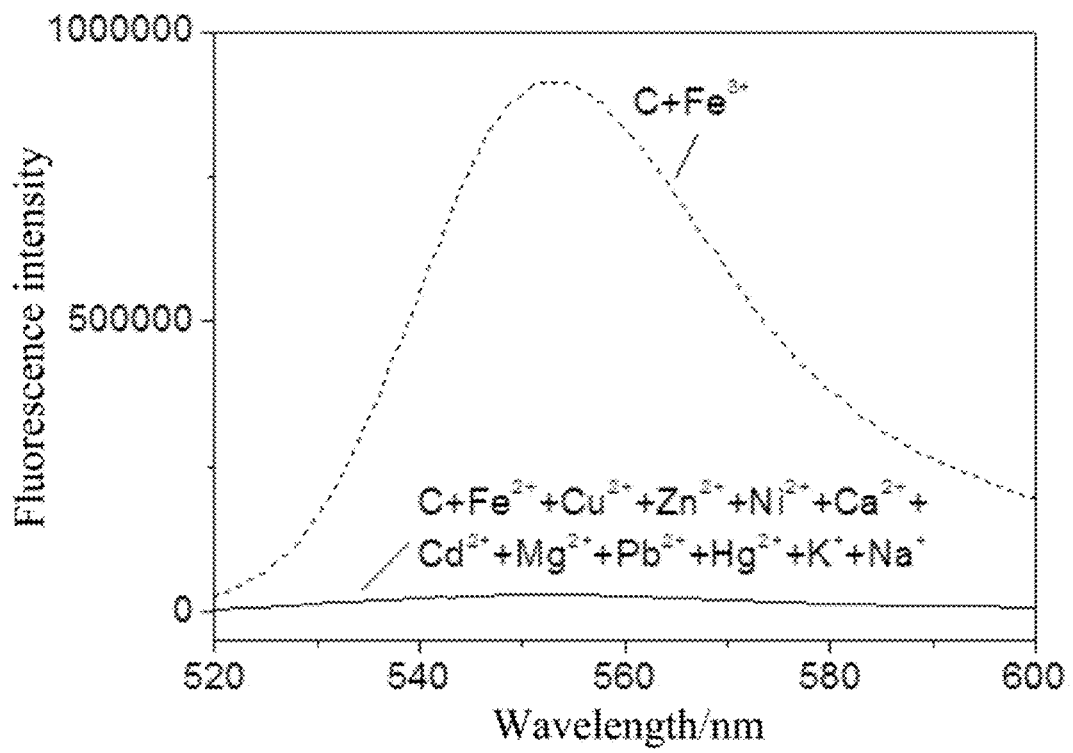
FIG. 1 is a fluorescence emission spectrum (excitation wavelength was 500 nm) of a solution after adding different metal ions to an aqueous solution of the water-soluble ferric ion fluorescent probe of the present invention.

To the parallel groups of water with a pH value of 7.0, the above precipitate C was added, respectively, $Fe^{3+}$, $Fe^{2+}$, $Cu^{2+}$, $Zn^{2+}$, $Ni^{2+}$, $Ca^{2+}$, $Cd^{2+}$, $Mg^{2+}$, $Pb^{2+}$, $Hg^{2+}$, $K^+$, and $Na^+$ were added to each group in turn, 5 μM each, and the last group was not added as a control group. The fluorescence emission spectra of each group (excitation wavelength was 500 nm) were measured. It was found that the fluorescence intensity was significantly enhanced after the addition of $Fe^{3+}$ compared with the control without ions; and the fluorescence intensity of the solution was substantially unchanged after the addition of other ions (as shown in FIG. 1). The results show that the precipitate C has excellent selectivity for $Fe^{3+}$.

2) Detection of Ferric Ion by the Ferric Ion Fluorescent Probe

Figure 2:
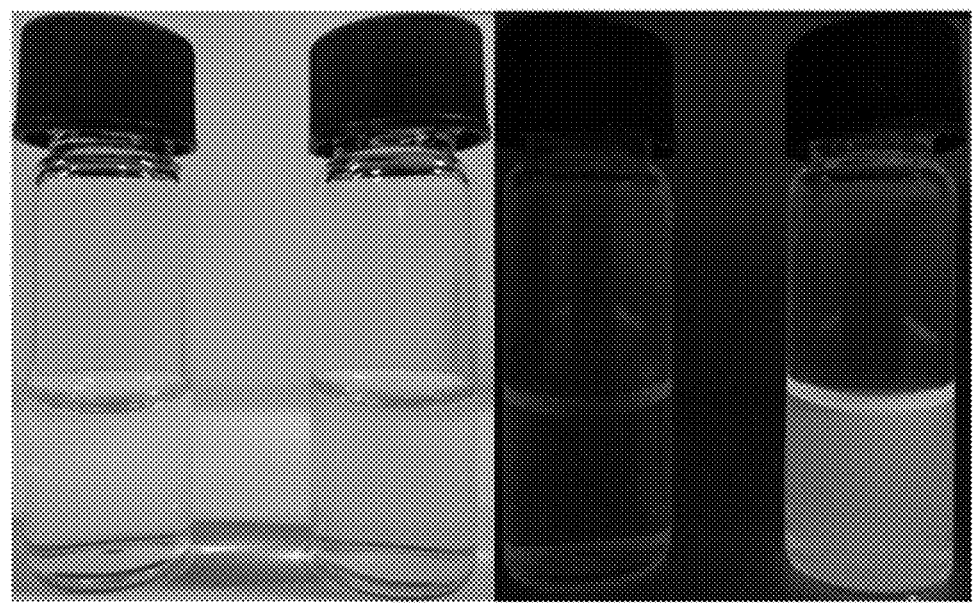
FIG. 2 is a photograph of two sample bottles under different light (left under sunlight, right under an ultraviolet lamp) (in both the bottles were aqueous solutions of the water-soluble ferric ion fluorescent probe of the present invention, the left bottle was not added with $Fe^{3+}$, and the right bottle was added with $Fe^{3+}$).

As shown in the left figure of FIG. 2, under the daylight, a water sample of the precipitate C was added to the sample bottle on the left, and the water sample in the sample bottle on the right was added with the precipitate C and $Fe^{3+}$. The two bottles were illuminated with an ultraviolet lamp, and the photograph in the right figure was obtained. It can be seen that the precipitate C was colorless and clear transparent in water, which proves that its water solubility is better than that of the general rhodamine-based fluorescent probe. On the other hand, the precipitate C changed from colorless to flesh pink when it encountered $Fe^{3+}$ in water, and the color change was very obvious and visible to the naked eye. It glowed bright yellow fluorescence under the illumination of an ultraviolet lamp. It can be seen that the detection of $Fe^{3+}$ by the precipitate C can be judged by the naked eye without using an instrument.

3) Cellular Experiment of the Ferric Ion Probe

Figure 3:
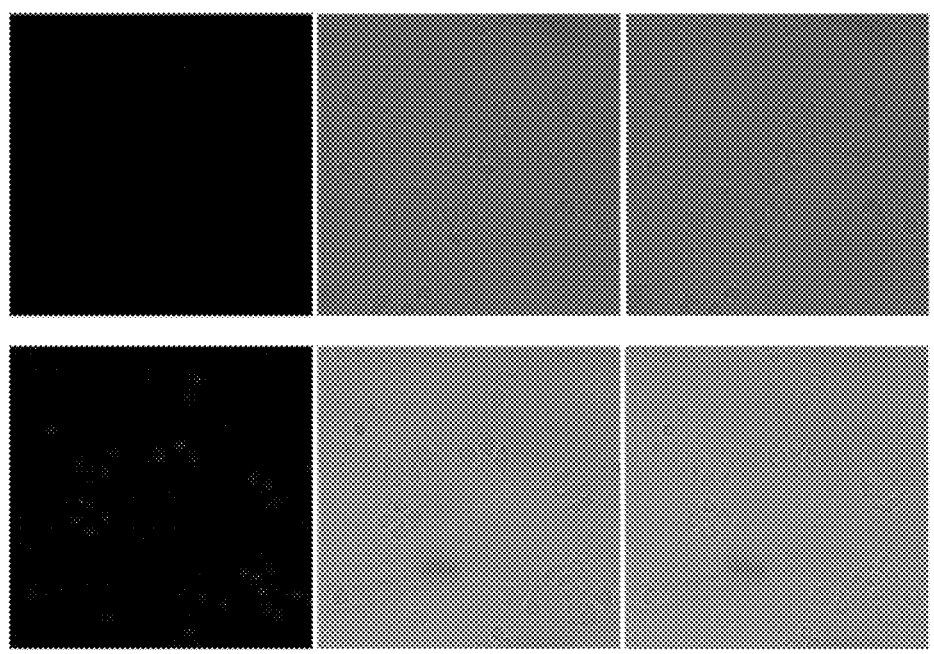
FIG. 3 is a confocal fluorescence photograph of HeLa cells after incubation for 5 h in medium containing different samples. Wherein, the first row of photographs are cells cultured only with the water-soluble ferric ion fluorescent probe of the present invention, and the second row of photographs are cells sequentially cultured with $Fe^{3+}$ and the water-soluble ferric ion fluorescent probe of the present invention. The first column is a fluorescent photograph, the second column is a bright field photo, and the third column is a superimposed photo of the first two columns.

HeLa cells were cultured in medium DMEM for 5 h in a 37° C. incubator, one group was added with $Fe^{3+}$ (10 μM) in the medium, and another group was not added with $Fe^{3+}$ as a control group. Then, $Fe^{3+}$ which did not enter the cells was washed away with a phosphate buffer solution having a pH value of 7.4, respectively. The two groups of cells were separately transferred to DMEM supplemented with C (10 μM) and further cultured. After 30 minutes, the cells were rinsed with a phosphate buffer solution and then observed with a confocal fluorescence microscopy. Fluorescence imaging of the two groups is shown in FIG. 3. It was found that almost no fluorescence was observed in the control group (the first row of photographs in FIG. 3), i.e., the cells which were not previously cultured with $Fe^+$, and the cells cultured in the medium containing $Fe^{3+}$ (see the second row of photographs in FIG. 3) showed fluorescence. The results show that the ferric ion fluorescent probe of the present invention is capable of penetrating the HeLa cell membrane to bind to $Fe^{3+}$ in the cell. This ability to penetrate cell membranes and the ability to enhance fluorescence due to binding to $Fe^{3+}$ may play an important role in monitoring the concentration of $Fe^{3+}$ in cells to study toxicity or biological activity in living cells.

The invention claimed is:
1. A water-soluble ferric ion fluorescent probe having the following structure:

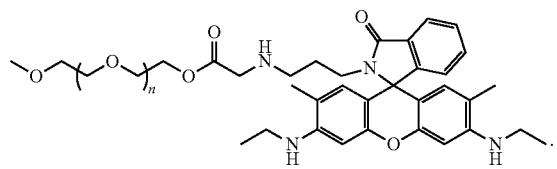

2. A method for preparing the water-soluble ferric ion fluorescent probe according to claim 1, comprising the following steps:
(1) using ethanol as a solvent, adding rhodamine 6G to a concentration of 0.02 mol/L to 0.2 mol/L, adding 1,3-propanediamine and reacting therewith, wherein the molar ratio of 1,3-propanediamine to rhodamine 6G is 0.5:1 to 10:1, controlling the reaction temperature at 40 to 80° C., and reacting for 4-9 h, cooling to precipitate a precipitate, and recrystallizing with acetonitrile to obtain a white crystal A;
(2) using dichloromethane as a solvent, adding methoxy polyethylene glycol MPEG2000 to a concentration of 0.025 mol/L to 0.25 mol/L, adding triethylamine in a molar ratio of triethylamine to methoxy polyethylene glycol MPEG2000 of 10:1 to 1:1, dropwise adding chloroacetyl chloride in a molar ratio of chloroacetyl chloride to methoxy polyethylene glycol MPEG2000 of 10:1 to 1:1, stirring in the dark overnight, precipitating in diethyl ether to obtain a product, dissolving the product in water, adjusting the pH value to 6, extracting 3 times with 20 ml of dichloromethane, and adding diethyl ether and washing to obtain a precipitate B; and
(3) using dichloromethane as a solvent, adding the white crystal A and the precipitate B in a molar ratio of 0.2:1 to 1:0.2, and adding KI in a molar ratio of KI to the white crystal A of 0.1:1 to 1:0.1, and adding potassium carbonate of 0.002 mol/L to 0.2 mol/L, reacting for 2-48 h, filtering, and adding filtrate to diethyl ether to precipitate a precipitate C which is the water-soluble ferric ion fluorescent probe.

* * * * *